United States Patent
Lincoln et al.

(10) Patent No.: US 10,702,403 B2
(45) Date of Patent: Jul. 7, 2020

(54) PROSTHETIC JOINT

(71) Applicant: OTTO BOCK HEALTHCARE GMBH, Duderstadt (DE)

(72) Inventors: Lucas Samuel Lincoln, Edmonds, WA (US); Ben Gilbert Macomber, Shoreline, WA (US); Nicholas Roy Corson, Mukilteo, WA (US); David Alan Boone, Seattle, WA (US)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 3 days.

(21) Appl. No.: 15/625,741

(22) Filed: Jun. 16, 2017

(65) Prior Publication Data
US 2017/0325974 A1    Nov. 16, 2017

Related U.S. Application Data (63) Continuation-in-part of application No. 15/536,240, filed as application No. PCT/US2015/066614 on Dec. 18, 2015.
(Continued)

(51) Int. Cl.
*A61F 2/66*    (2006.01)
*A61F 2/68*    (2006.01)
(Continued)

(52) U.S. Cl.
CPC .............. *A61F 2/6607* (2013.01); *A61F 2/66* (2013.01); *A61F 2/68* (2013.01);
(Continued)

(58) Field of Classification Search
CPC ... A61F 2/66; A61F 2/6607; A61F 2002/5006
See application file for complete search history.

(56) References Cited

U.S. PATENT DOCUMENTS

| 2,638,605 A | 5/1953 | Johnson |
| 5,957,981 A * | 9/1999 | Gramnas ............... A61F 2/6607 |
| | | 623/47 |

(Continued)

FOREIGN PATENT DOCUMENTS

| CN | 2614648 Y | 5/2004 |
| CN | 2614650 Y | 5/2004 |

(Continued)

OTHER PUBLICATIONS

PCT International Search Report for corresponding PCT International Patent Application No. PCT/US2015/066614, dated Jun. 3, 2016.

*Primary Examiner* — Bruce E Snow
*Assistant Examiner* — Melissa A Hoban
(74) *Attorney, Agent, or Firm* — Holland & Hart, LLP (57) ABSTRACT

A prosthetic joint and a method of controlling dorsiflexion and plantarflexion of the hydraulic prosthetic ankle joint. The method includes generating ground reaction forces with a hydraulic prosthetic ankle, wherein the prosthetic hydraulic ankle comprises a first chamber and a second chamber, and the ankle is connected to a prosthetic foot; rotating the prosthetic foot in response to the ground reaction force; transferring fluid between the forward and rear chambers in response to rotation of the foot; providing a feature to occlude or partially occlude the fluid transfer between chambers; providing a non-electronic mechanism for controlling the flow responsive to both a position of the joint and a rate of change of position of the joint, and wherein the mechanism is arranged such that a dwell at a particular joint location or locations will occlude the flow path.

15 Claims, 12 Drawing Sheets

Related U.S. Application Data (60) Provisional application No. 62/094,009, filed on Dec. 18, 2014.

(51) Int. Cl.
 *A61F 2/50* (2006.01)
 *A61F 2/74* (2006.01)
 *A61F 2/76* (2006.01)

(52) U.S. Cl.
 CPC . *A61F 2002/5006* (2013.01); *A61F 2002/745* (2013.01); *A61F 2002/747* (2013.01); *A61F 2002/748* (2013.01); *A61F 2002/7615* (2013.01)

(56) References Cited

U.S. PATENT DOCUMENTS

| | | | |
|---|---|---|---|
| 6,106,560 A | 8/2000 | Boender | |
| 6,113,642 A | 9/2000 | Petrofsky et al. | |
| 7,985,265 B2* | 7/2011 | Moser | A61F 2/6607 623/50 |
| 8,298,294 B2* | 10/2012 | Kaltenborn | A61F 2/6607 623/26 |
| 8,500,824 B2 | 8/2013 | Okuda et al. | |
| 8,628,585 B2* | 1/2014 | Harris | A61F 2/6607 623/27 |
| 8,974,543 B2* | 3/2015 | Balboni | A61F 2/60 623/43 |
| 8,986,398 B2* | 3/2015 | Poulson, III | A61F 2/6607 623/52 |
| 9,114,029 B2* | 8/2015 | Sgeirsson | A61F 2/6607 |
| 2007/0233279 A1 | 10/2007 | Kazerooni et al. | |
| 2008/0262635 A1* | 10/2008 | Moser | A61F 2/6607 623/47 |
| 2009/0030530 A1* | 1/2009 | Martin | A61F 2/6607 623/53 |
| 2010/0191347 A1 | 7/2010 | Pusch et al. | |
| 2013/0173022 A1 | 7/2013 | Arabian et al. | |
| 2014/0128993 A1* | 5/2014 | Shen | A61F 2/68 623/44 |
| 2014/0379096 A1* | 12/2014 | Zahedi | A61F 2/66 623/25 |
| 2015/0134081 A1 | 5/2015 | Geiger et al. | |

FOREIGN PATENT DOCUMENTS

| | | |
|---|---|---|
| CN | 101959477 A | 1/2011 |
| WO | 2014057086 A1 | 4/2014 |
| WO | 2016100791 A1 | 6/2016 |

* cited by examiner

PROSTHETIC JOINT

CROSS-REFERENCE TO RELATED APPLICATIONS

This is a continuation-in-part of U.S. patent application Ser. No. 15/536,240, filed 15 Jun. 2017, which was filed as a national stage application of PCT International Application No. PCT/US2015/066614, filed 18 Dec. 2015, and claims the benefit of U.S. Provisional Application No. 62/094,009, filed 18 Dec. 2014, the entire disclosures of which are incorporated herein, in their entireties, by this reference.

BACKGROUND

The field of prosthetics has seen many advances to enhance quality of life by improving mobility and returning functionality to persons suffering from injured or missing limbs. Prostheses attempt to mimic the movements of the limb that they replace. For example, a healthy functioning ankle will go through a series of plantarflexion and dorsiflexion motions during gait without the person having to consciously control the ankle movement. Therefore, improvements have been sought to produce prosthetic ankle joints that may mimic the movements of a healthy ankle to improve the patient's comfort and functionality.

A prosthetic ankle joint must exhibit sufficient dorsiflexion and plantarflexion dampening when the patient walks to permit the most natural gait possible. On the other hand, when the prosthesis user is standing, sufficient stability and support must be achieved to permit a stable stance. It is therefore necessary that the prosthesis is operated in two different states, i.e., for walking on the one hand and for standing on the other hand. To build the prosthesis lightweight, with little susceptibility to faults, low costs and energy savings, the prosthesis should be able to do without electronic control elements. Different prosthetic ankle joints are known having two separate cylinders interconnected via a fluid passage. During movement of the ankle, fluid is guided from one cylinder into the other cylinder. The fluid resistance in this fluid passage is responsible for a dampening of the joint. However this type of ankle joint requires significant space, making it difficult, if not impossible, to arrange this kind of ankle joint in a decorative foot cover.

SUMMARY

The present disclosure is directed to a prosthetic joint, and particularly a prosthetic ankle joint, as well as methods for its control, that mitigates or removes the disadvantages described above. An artificial ankle joint according to the present disclosure comprises a foot connector, a lower leg connector and a fluid system, wherein the lower leg connector and the foot connector are pivotable about an axis of rotation with respect to each other. The fluid system includes a first cylinder and a first piston movably positioned inside the first cylinder, and a second cylinder and a second piston movably positioned inside the second cylinder. The first cylinder and the second cylinder are connected via a fluid connection and are arranged such that a fluid is moved from one of the first cylinder and the second cylinder into the other of the first cylinder and the second cylinder by pivoting the foot connector relative to the lower leg connector around the axis of rotation. The first cylinder and the second cylinder are positioned posterior of the axis of rotation.

By positioning both cylinders posterior of the axis of rotation at least two effects are achieved. First, the space needed for the artificial ankle joint is reduced. Second, it becomes possible to arrange the axis of rotation further in the direction of the forefoot compared to other artificial ankle joints. The forefoot here refers to a forefoot of a foot being connected or connectable to the foot connector of the artificial ankle joint.

Positioning the axis of rotation further in the direction of the forefoot reduces the pressure inside the fluid system when there is weight on the forefoot. A lever, which transmits the force from the forefoot of the artificial foot to the axis of rotation, is shorter compared to other artificial ankle joints. At the same time, the lever that is effective during heel strike gets lengthened, and the maximum pressure in this phase of a gait cycle is smaller than when weight is placed on the forefoot. The maximum pressure occurring during a gait cycle may be reduced with the positioning of the first cylinder and the second cylinder according to the present disclosure.

The fluid system may also comprise a reservoir being coupled in flow communication to both cylinders. This reservoir may be used to balance fluctuations and variations of pressure inside the fluid system. These pressure variations may occur due to thermal expansion of the fluid. The reservoir may be a closed volume that is connected to the other parts of the fluid system via a fluid connection. The volume may be limited on at least one side by a spring or a wall onto which a spring applies its force.

Additionally, or as an alternative, an elastic membrane may be used. These elements apply a certain amount of pressure onto the fluid inside the volume of the reservoir. This pressure is transmitted via the fluid connection to the fluid in both cylinders. Hence, the fluid system is at least almost free of play. Preferably, the fluid system is completely free of play. This is particularly advantageous if, for example, the fluid inside the fluid system expands or contracts due to temperature differences or temperature changes. The resulting change in volume may be balanced by the reservoir.

At least one of the first cylinder and the second cylinder may be a rotary cylinder. Of course, both of the first cylinder and the second cylinder may be rotary cylinders. Alternatively the first cylinder and the second cylinder are arranged such that the first piston and the second piston abut with a contact element at a contact surface, wherein the first piston and the second piston, and thus the first cylinder and the second cylinder, are positioned at an angle of 180°. The first cylinder may have its opening at its underside and the second cylinder may have its opening at the top. Preferably, the first piston and the second piston project with their respective contact element from the respective cylinder and can thus be positioned at the corresponding contact surface positioned at the foot connector or the lower leg connector, respectively.

The prostatic ankle joint may include a non-electronic controlling device arranged to control an amount of fluid that is moved from one of the first cylinder and the second cylinder into the other of the first cylinder and the second cylinder depending on at least one of a position or a change of position of the foot connector relative to the lower leg connector. With this device, a dynamic dampening may be achieved depending on the position of the foot connector relative to the lower leg connector. Additionally, or alternatively, the dampening may also be dependent on the velocity of the change of the angle between the foot connector and the lower leg connector, which is defined to be the rotation velocity.

A prosthetic ankle joint design according to one embodiment of the present disclosure may provide functionality in two different states. In a first state, such a joint is adapted to provide a dynamic, controlled-resistance walking gait. In the second state, the joint is adapted to provide a static, fully supported standing state. The fluid system may be a hydraulic system or a pneumatic system. The regulated prosthetic joint according to this embodiment enables both of these states without activation of each state through a microprocessor and without sacrificing standing stability in favor of a dynamically performing ankle during gait.

During walking gait, the healthy human ankle covers a range of about 30 degrees through a series of controlled dorsiflexion and plantarflexion periods. During standing, the ground-reaction-force (GRF) supporting body weight is located in the mid-food, and directionally travels to the interior side of the ankle joint. This creates a moment on the ankle joint that must be counteracted to attain stability. In healthy ankles, the ankle is supported by the plantar flexor muscles. In mechanical prosthesis, it has been known to counteract the moment using a mechanical support, such as a rigid attachment. In a hydraulically damped ankle, this moment is not supported, leading to unstable and unsatisfactory performance of the ankle for the very common task of standing.

The prosthetic joint according to one embodiment may have the advantage that the joint may be used as an ankle. The joint has a passive, mechanical response system to control the walking and standing states that mimics a naturally functional joint. The prosthetic ankle joint provides dorsiflexion and plantarflexion that mimics the movements of a natural ankle when walking and also provides support when standing.

The controlling device of the prosthetic joint may include an occlusion or valve configured to restrict fluid flow between the cylinders. The occlusion is arranged such that a dwell at a particular joint location or locations will result in occlusion the flow path.

The prosthetic joint or prosthesis joint may be a prosthetic ankle joint. The two "connectors" are connected pivotally to each other via a joint that can take nearly any known form. These parts may, for example, be functional parts of the ankle joint, i.e., for example a sole part or an attachment element for a lower leg part, or additional elements to which further parts of the prosthesis joint may be attached. The parts are aligned with each other and pivot via an ankle area that covers at least the area that is needed for the respective prosthesis joint, and particularly for the prosthetic ankle joint.

The two cylinders define a first chamber and a second chamber, respectively, which are filled with a fluid and connected to each other flow-technically via the fluid connection.

When the position of the joint is changed, i.e., when the first and the second connector are pivoted relative to each other so that an enclosed angle changes, this will cause the fluid from one of the two chambers to flow into the respective other one. A specific position of the two connectors relative to each other is subsequently also called the joint position or location of the joint.

The "occlusion" may be formed as a throttle element or a closure element. It limits the amount of fluid that can flow through the fluid flow path.

The closure is controlled by a non-electronic control system or a non-electronic control device that reacts to either or both of the position of the joint and the speed of the change of position. To close the fluid connection, the joint remains in a predetermined position or a predetermined position range for a predetermined period. This position may correspond to the position that the joint holds when the wearer of the prosthesis of which the joint is a part is standing. In this position, the control mechanism causes the closure to close the fluid connection if the joint remains in this position for a predetermined period. This is usually only the case when the patient is standing with the joint. When walking, the joint also goes through this position, but will not remain there beyond the predetermined duration, so that there will be no closing.

The fluid connection between the first cylinder and the second cylinder may be open or occluded using a mechanical device, such as a cam linked to a valve. The joint may be rotatably coupled to a foot. The joint response to walking and rotation of the foot is to adjust the resistance to flow between actuators as the foot experiences the ground reaction forces starting from heel strike, mid-stance, and push off. During push-off there is particular weight on the forefoot. However, the resistance is not the same throughout the stance phase, but varies with the rotational position and the rate of rotation. The progression of dampening and of the resistance opposing the occurring force may be adjusted freely in a wide range by the shape of the cam connected to the valve.

In some embodiments, the joint comprises a bi-directional flow path with a variable occlusion that connects the chambers and a uni-directional flow path that connects the chambers, and further comprises applying a damping force on the occlusion when acted upon by the external forces to delay restriction to fluid flow.

In some embodiments, the joint comprises a bi-directional flow path with a variable occlusion that connects the chambers and a uni-directional flow path that connects the chambers, and further comprises providing 100% of the forces that drive the occlusion to restrict flow from the ground reaction forces.

In some embodiments, the joint includes a contact surface in the form of a cam driving a contact element in the form of a follower, and the follower position drives closure of a valve against an opposing damping element to restrict fluid flow. In some embodiments, the cam induces a dwell period during at least one portion of rotation during which the cam drives the valve to fully close at or before the mechanism dynamics cease. In some embodiments, the joint includes a magnetic element, and the magnetic element drives the closure of a valve against an opposing damping element to restrict fluid flow. In some embodiments, a magnetic force at a predetermined joint location fully closes the valve at or before the closure mechanism reaches a steady-state.

In some embodiments, fluid transfer is restricted when standing at a particular angle of the joint for a period of time determined by a damping element. In some embodiments, when a center of gravity of a body supported by the joint is anterior of the pivot location and the mechanism has occluded the flow path, the rate of rotation is zero. In some embodiments, the occlusion is connected to a damping element that opposes movement of the occlusion when the occlusion moves to restrict fluid flow between chambers. In some embodiments, the joint further comprises a cam driving a follower, and the follower position drives closure of the occlusion through a compliant element. In some embodiments, the cam shape provides simple harmonic motion. In some embodiments, the cam and occlusion mechanism are configured to occlude the passage between the first and second cylinders when the joint is stopped, or nearly stopped, at a particular angular location for a period of time defined by the mechanism dynamics.

In some embodiments, the joint includes a magnetic element, and the magnetic element drives the closure of the occlusion against an opposing damping element. In some embodiments, a magnetic force at a predetermined joint location, i.e., the closing position, fully closes the valve at or before the mechanism reaches a steady state. In some embodiments, the joint comprises a bi-directional flow path connecting the first and second chambers. In some embodiments, the joint comprises a uni-directional flow path connecting the first and second chambers.

The joint may have at least one piston that is at least partially placed in the first chamber and/or in the second chamber and moved by movement of the first connector relative to the second connector so that fluid from one chamber is moved to the other chamber. It may be advantageous if fluid is moved from the first chamber into the second chamber during a movement of the joint into one direction, e.g., at dorsiflexion, while fluid will be moved from the second chamber into the first chamber in the opposite movement of the joint, i.e., plantarflexion.

It has turned out to be beneficial if the dampening element against which the closure may be moved into the closed position, is also a hydraulic or pneumatic dampening element or a dampening element filled with a different fluid. Thus, the closure may be, e.g., a needle valve, the needle of which is pushed into the fluid connection to close the fluid connection and to put the valve from the "walking" to the "standing" mode. For this, a part of the valve to which the needle belongs, must be pushed into a volume that has a fluid connection to a dampening chamber and a dampening piston. The dampening element may have at least one dampening chamber and at least one dampening piston, which is actuated in a predetermined range of the position of the first connector relative to the second connector to prevent closing of the fluid connection.

The fluid connection between the one area of the closure and the dampening chamber may be used to set the strength of the dampening applied by the dampening element. A throttle valve or similar device may be present for this as well. The dampening piston that closes the dampening chamber off to one side may have an actuation element that may interact with the cam or an element attached to it. This may be of particular benefit when a large force is applied to the closure in an extreme position of the joint, i.e., at strong pivoting of the first connector relative to the second connector, which alone would be sufficient to close the fluid connection between the first chamber and the second chamber relatively quickly. Since this may not be desired in this position, however, there may be an actuation element at the dampening piston for this case. The dampening piston is then pushed towards the dampening chamber and thus pushes the fluid in it through the further fluid connection towards the closure, thus preventing closing of the fluid connection between the two chambers.

In some embodiments, a prosthetic system includes the prosthetic joint of any of the above embodiments, a prosthetic foot connected to the joint at one of the connectors, and the second connector is connected to a prosthetic device including a socket to receive a limb.

In some embodiments, a method of controlling rotation of a prosthetic joint includes applying an external force that causes rotation of a joint, wherein the joint comprises a first and second chamber, transferring fluid between the first and second chambers in response to rotation of the joint, providing a feature to occlude or partially occlude the fluid between chambers, and providing a non-electronic mechanism for controlling the flow responsive to both a position of the joint and a rate of change of position of the joint. The mechanism is arranged such that a dwell at a particular joint location or locations will occlude the flow path.

In some embodiments, a method of controlling dorsiflexion and plantarflexion of a hydraulic prosthetic ankle joint includes generating ground reaction forces with a hydraulic prosthetic ankle, wherein the prosthetic hydraulic ankle comprises a first chamber and a second chamber, and the ankle is connected to a prosthetic foot, rotating the prosthetic foot in response to the ground reaction force, transferring fluid between the forward and rear chambers in response to rotation of the foot, providing a feature to occlude or partially occlude the fluid transfer between chambers, and providing a non-electronic mechanism for controlling the flow responsive to both a position of the joint and a rate of change of position of the joint. The mechanism is arranged such that a dwell at a particular joint location or locations will occlude the flow path.

The fluid flow path may be opened again in the method by application of a torque onto the first connector or the second connector in a predetermined direction. This way, it is possible to return the joint from the operating mode "standing" to the operating mode "walking".

A force may be applied using the torque onto the fluid that is thus moved by the one-way connection from one chamber to the respective other chamber, which releases the lock applied by the closure.

The embodiments of the joint may rely on the use of a non-electronic mechanism for controlling the flow responsive to both a position of the joint and a rate of change of position of the joint, wherein the mechanism is arranged such that a dwell at a particular joint location or locations will occlude fluid flow. The mechanisms can operate using the ground reaction forces, such as when walking, standing, or sitting, for example, or from changing positions. A mechanism that can control fluid flow via the use of non-electrical components may reduce the overall size due to elimination of a power source.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 6 shows the sectional view of FIG. 2 through a further execution example of the present disclosure.

DETAILED DESCRIPTION

Figure 1:
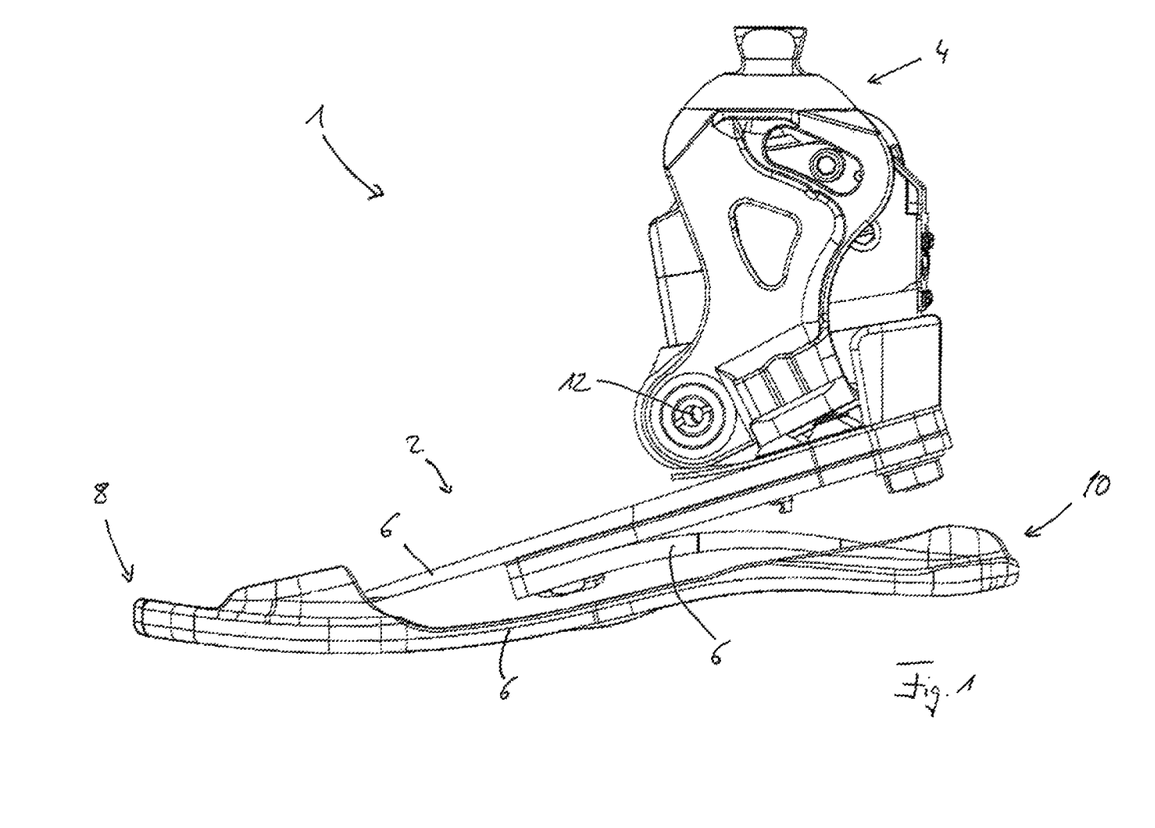
FIG. 1 is a side view of a prosthetic ankle joint in accordance with the present disclosure.

FIG. 1 shows a prosthetic ankle joint 1, on which a foot part 2 and a lower leg part 4 are located. For the purposes of the present disclosure, a foot part 2 does not have to be, as shown in FIG. 1, a complete prosthetic foot. It is sufficient if a foot part 2 has a fastening device for such a foot. The same applies to a lower leg part 4, which must likewise only contain a fastening element for a further prosthetic lower leg.

Figure 2:
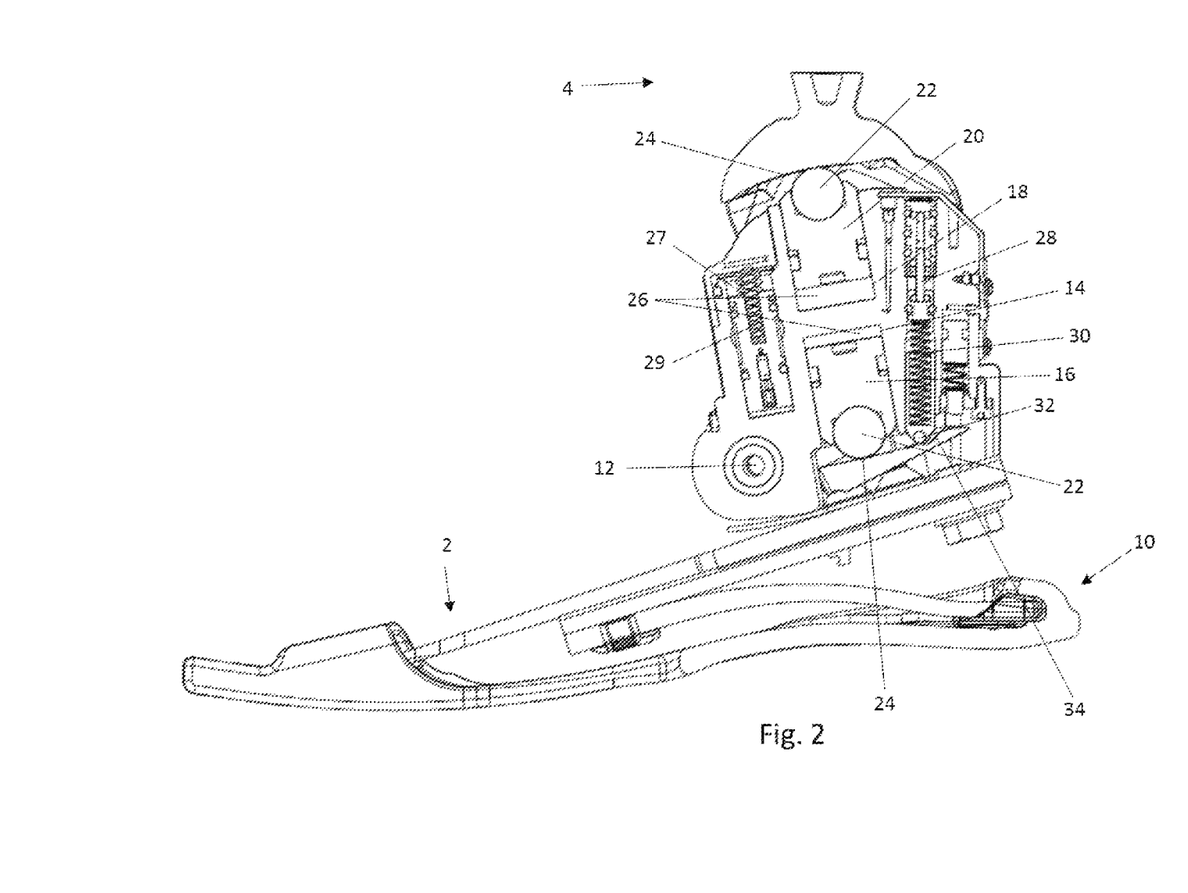
FIG. 2 is a sectional view through the joint of FIG. 1.

FIG. 2 shows a sectional view of the prosthetic ankle joint of FIG. 1. A first cylinder 14 with a first piston 16 movable therein, and a second cylinder 18 with a second piston 20 movable therein, are shown in FIG. 2. The two pistons 16, 20 each have an abutment element 22, which rests against a contact surface 24 in each case. Both cylinders 14, 18 are displaced posteriorly, i.e., in the direction towards the heel area 10 relative to the axis of rotation 12.

A fluid-filled volume 26, which size changes, is located in each of the two cylinders 14, 18 when the foot part 2 is pivoted relative to the lower part 4 around the axis of rotation 12. In order to be able to compensate for pressure and/or volume fluctuations (caused by, for example, temperature changes), and to avoid play and hence rattling noises, the ankle joint 1 may have a reservoir 27. The reservoir 27 may be pre-tensioned by a pre-stressing element 29, i.e., a spring.

FIG. 2 illustrates a control mechanism is located to the right of the two cylinders 14, 18. The control mechanism has a closing element 28 which is designed to be displaceable upwards and downwards in the embodiment shown. The closing element 28 is coupled with a damping element 30, which is designed as a helical spring in the exemplary embodiment shown. On the underside of the damping element 30 is a contact element 32, which rests against a contact surface 34.

Figure 3:
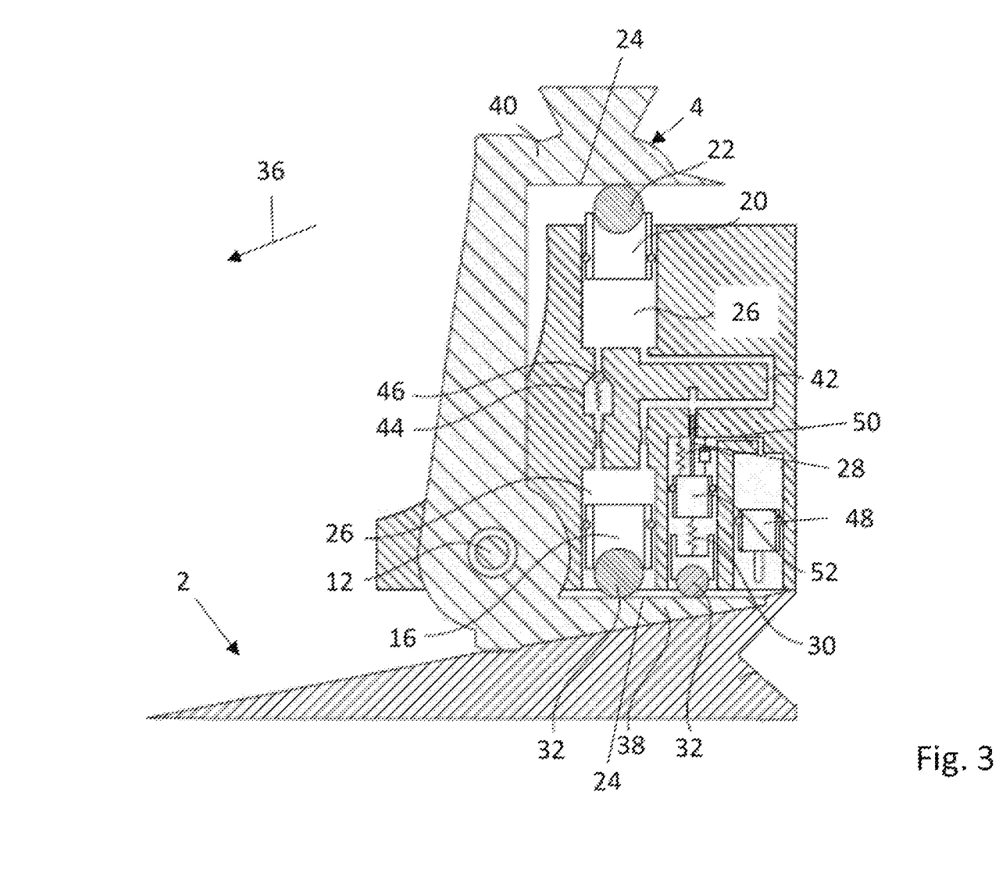
FIG. 3 is a schematic view of a prosthetic ankle joint in accordance with the present disclosure.

FIG. 3 shows the structure of the prosthetic ankle joint 1 of FIGS. 1 and 2 schematically. The foot part 2 and the lower leg part 4 are pivotable about the axis of rotation 12. When the lower leg part 4 is pivoted relative to the foot part 2 along the arrow 36, the angle between the foot part 2 and the lower leg part 4 decreases so that it is a plantarflexion movement. In this case, a lower contact surface 24, which is part of a lower swivel arm 38, is moved up, thus also displacing the abutment element 32 and the first piston 16 upward, thereby reducing the volume 26 above the first piston 16. At the same time, an upper swivel arm 40 is also tilted, as a result of which the contact surface 24, which is located on the upper swivel arm 40, and thus also the abutment element 22 moves upward in the exemplary embodiment shown. As a result, the second piston 20 is also pivoted within the second cylinder 18, thereby increasing the volume 26 in this cylinder.

The contact element 32, which is part of the control mechanism, is connected to the clasping element 28 via the damping element 30 and is pressed upwards as far as the foot performs a plantar flexing movement. As a result, a fluid connection 42 between the first cylinder 14 and the second cylinder 18 is closed. A second fluid connection 44 is closed by a corresponding one-way valve 46, so that movement of the fluid is only possible in one direction.

In the exemplary embodiment shown in FIG. 3, the ankle joint 1 has an actuating element 48, which can be displaced in the cylinder in which it is arranged. For this purpose, the actuating element 48 may be brought into contact with the posterior end of the lower pivot arm by a corresponding movement of the foot part 2 relative to the lower leg part. Using a pumping line 50, a fluid is pressed into the region above a piston 52 so that the piston 52 is moved downwards. The piston 52 is connected to the closing element 28 such that moving the piston 52 also moves the closing element 28 downwards, thus opening the fluid connection.

Figure 4:
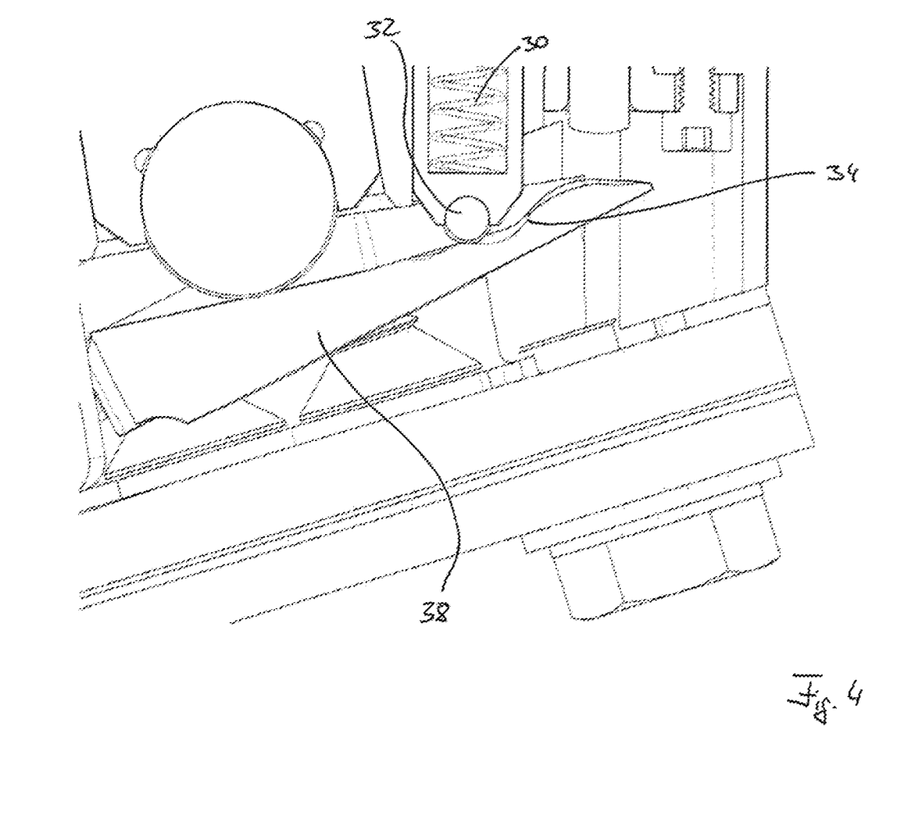
FIG. 4 is an enlarged section from FIG. 2.

FIG. 4 shows an enlarged section from FIG. 2. The contact element 32 and the contact surface 34, which is designed to be curved, can be seen. In contrast to the schematic representation in FIG. 3, a pivoting of the lower swivel arm 38 does not result in a monotonous movement of the contact element 32 along the contact surface 34 in only one direction, but may cause a reciprocating movement. This reciprocating movement is damped via the damping element 30, so that the closing element (not shown in FIG. 4) does not follow this movement directly.

Figure 5:
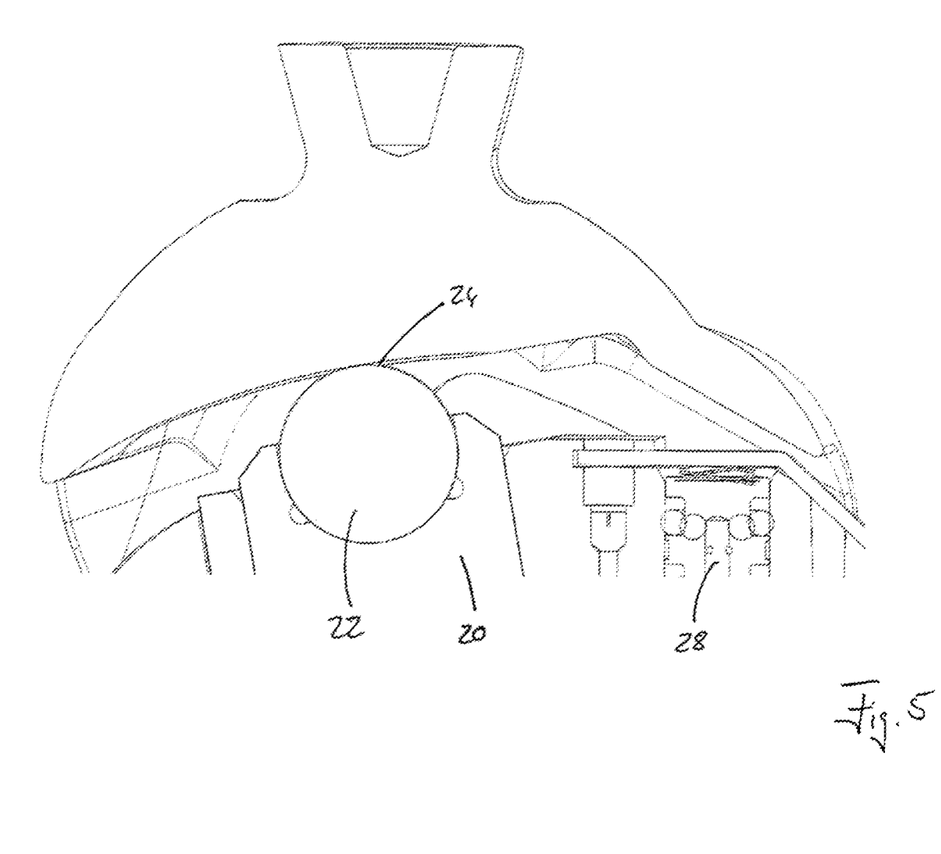
FIG. 5 is an additional enlarged section from FIG. 2.

FIG. 5 shows a further section from FIG. 2. An upper end of the closing element 28 can be seen, which, if the foot part 2 and the lower part 4 take the closed position, are pushed upwards and the fluid connection 42 is closed. The abutment element 22 of the second piston 20 bears against a contact surface 24.

FIG. 6 shows a further embodiment of the present disclosure in which the reservoir 27 and the corresponding pre-stressing element 29 are arranged differently. This arrangement may result in a different form of the space required, which may be advantageous for certain forms of a cosmetics surrounding of the shown foot part.

Figure 7:
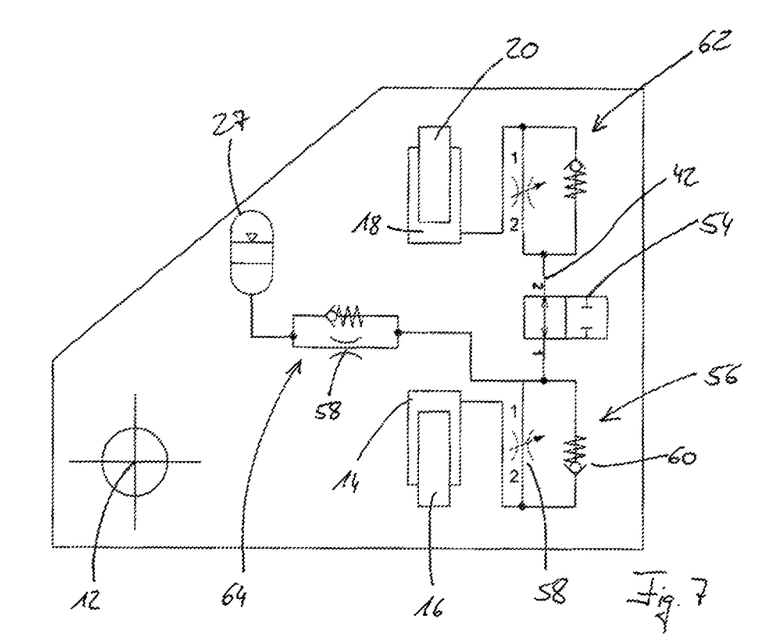
FIGS. 7-12 show schematic views of various fluid circuits in accordance with the present disclosure.

FIG. 7 shows a schematic representation of the fluid circuit used for another exemplary embodiment of the present disclosure. The axis of rotation 12, the first cylinder 14 with the first piston 16 located therein, and the second cylinder 18 with the second piston 20 can be seen. The device has a reservoir 27. In the exemplary embodiment shown, there is also a valve 54, which is designed as a two-way valve. In the position shown in FIG. 7, the fluid connection 42 between the first cylinder 14 and the second cylinder 18 is opened. If the valve 54 is moved to the second position, this connection is interrupted and the ankle joint is blocked.

A first damping device 56 is located between the valve 54 and the first cylinder 10. The first damping device 56 has an adjustable throttle 58 and a spring-loaded backflow valve 60. A second damping device 62 is located between the valve 54 and the second cylinder 18. The second damping device 62 is constructed analogously to the first damping device 56. A further, third damping device 64 is located between the fluid connection 42 and the reservoir 27, however, this has only one non-adjustable throttle 58. A resistance that is counteracted by the fluid system of a pivoting of the ankle joint and a pivoting of the foot part relative to the lower leg part 4 can be set by adjusting the two adjustable throttles 58 of the first damping device 56 and of the second damping device 62.

Figure 8:
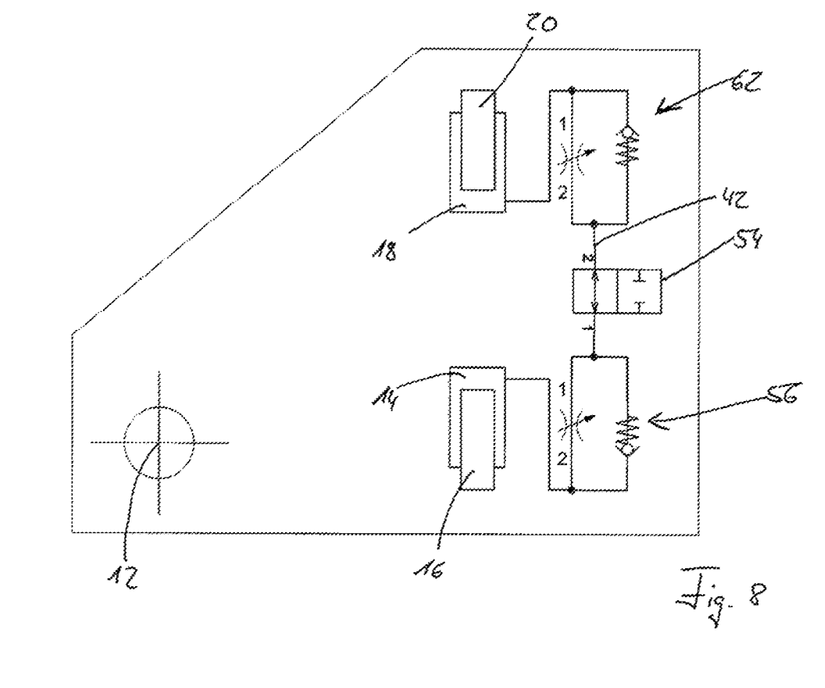

FIG. 8 shows a further exemplary embodiment of the present disclosure. In this case, the fluid system between the two cylinders 14, 18 has a valve 54, which may close and open the fluid connection 42 as well as the first damping device 56 and the second damping device 62. The fluid system may or may not include a reservoir 27 as shown in FIG. 7.

Figure 9:
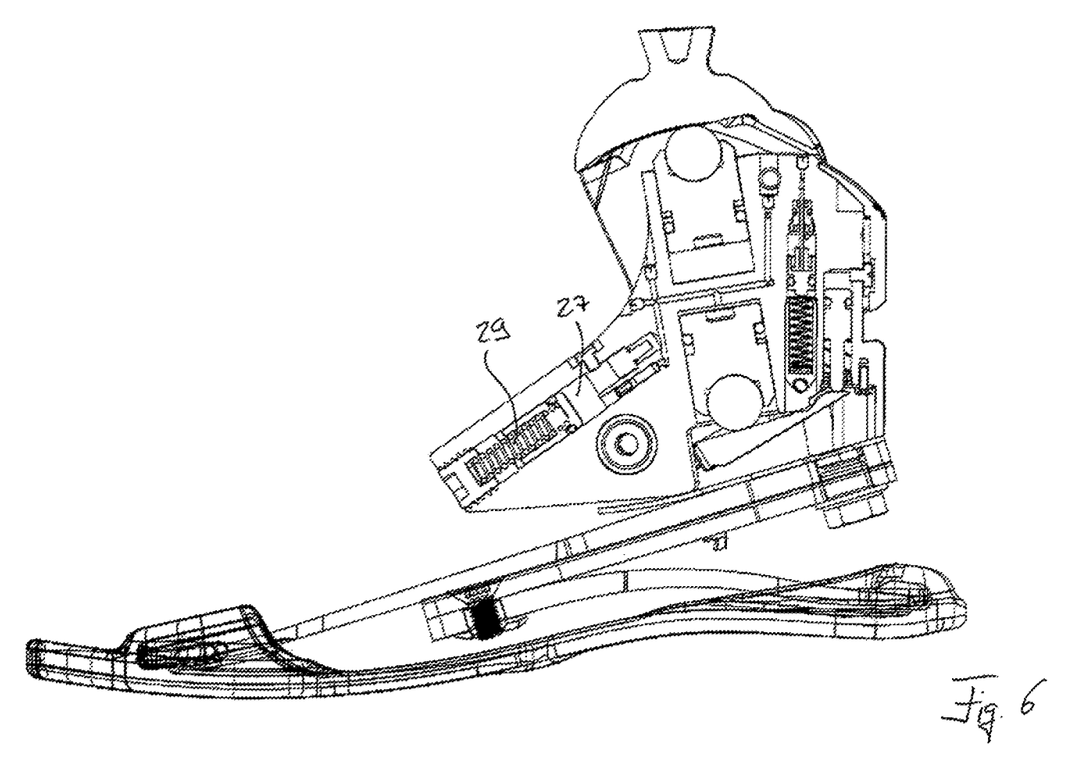

FIG. 9 shows an embodiment in which there is only the first damping device 56 between the first cylinder 14 and the second cylinder 18. The second cylinder 18 may include the adjustable throttle 58, but does not contain a backflow valve 60. In this way, the damping effect which is opposed to a dorsiflexion and a plantarflexion typically cannot be adjusted separately, but may be identical for both directions of movement. The embodiment of FIG. 9 includes a reservoir 27, which is coupled to the fluid connection 42 via the third damping device 64.

Figure 10:
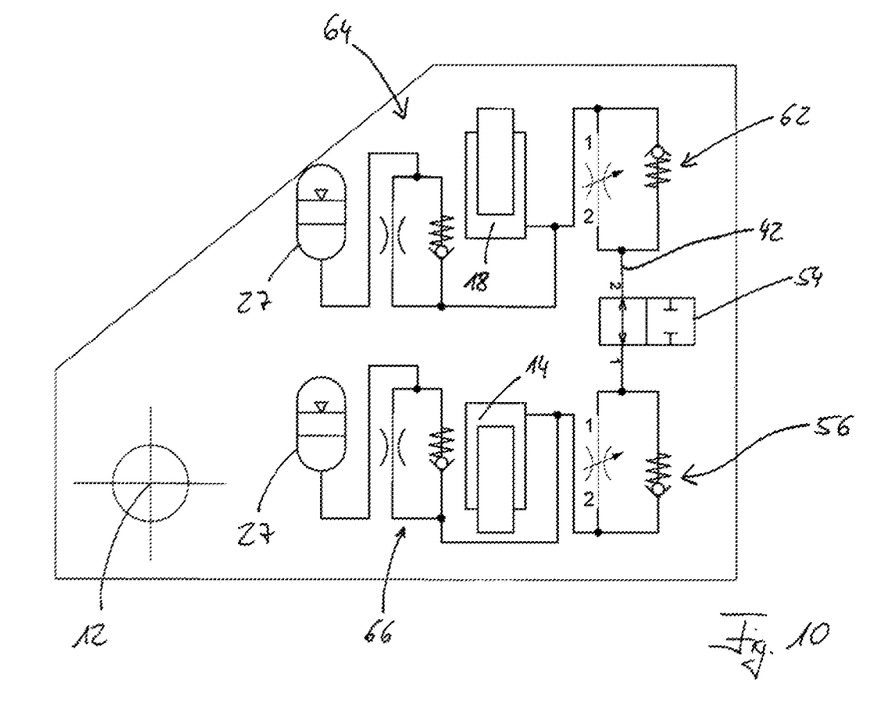

FIG. 10 shows an embodiment in which the first damping device 56 is arranged between the valve 54 and the first cylinder 14, and the second damping device 62 is arranged between the valve 54 and the second cylinder 18. Unlike the other embodiments disclosed above, the embodiment shown in FIG. 10 has two separate reservoirs 27 which are connected to the fluid connection 42 between the first piston 14 and the second piston 18 via a third damping device 64 and a fourth damping device 66.

Figure 11:
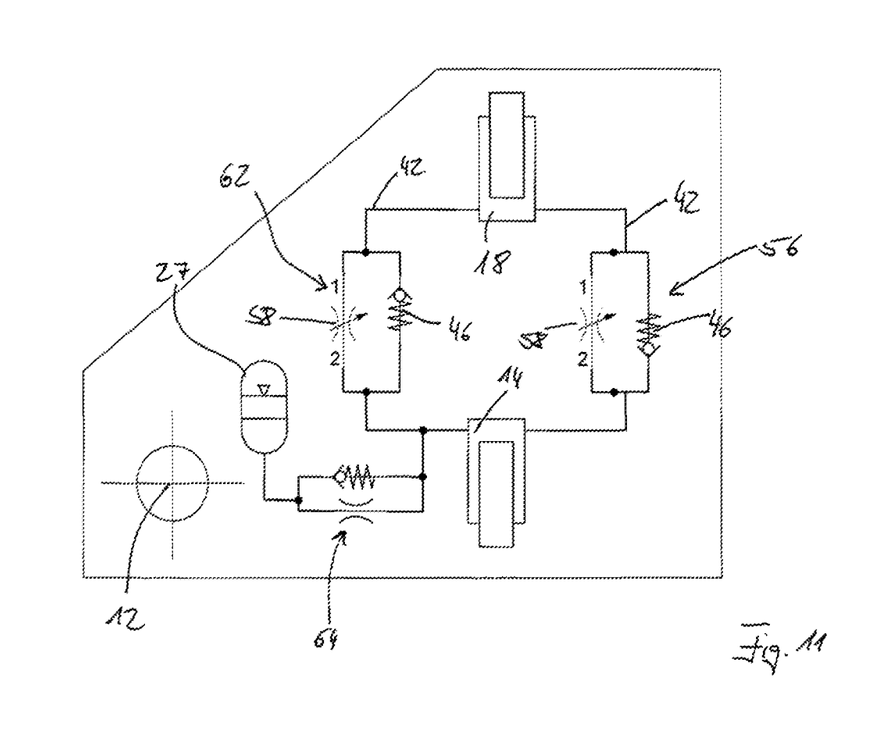

FIG. 11 shows a further embodiment having two fluid connections 42, in which the first damping element 56 and the second damping element 62 are located. The fluid connections 42 are arranged between the first cylinder 14 and the second cylinder 18. Two one-way valves 46 are arranged in such a way that the respective throttles 58 are either active during a dorsiflexion movement or a plantarflexion movement, so that the two movements may be dampened to different degrees, if this is desired. The reservoir 27 is again coupled via the third damping device 64.

Figure 12:
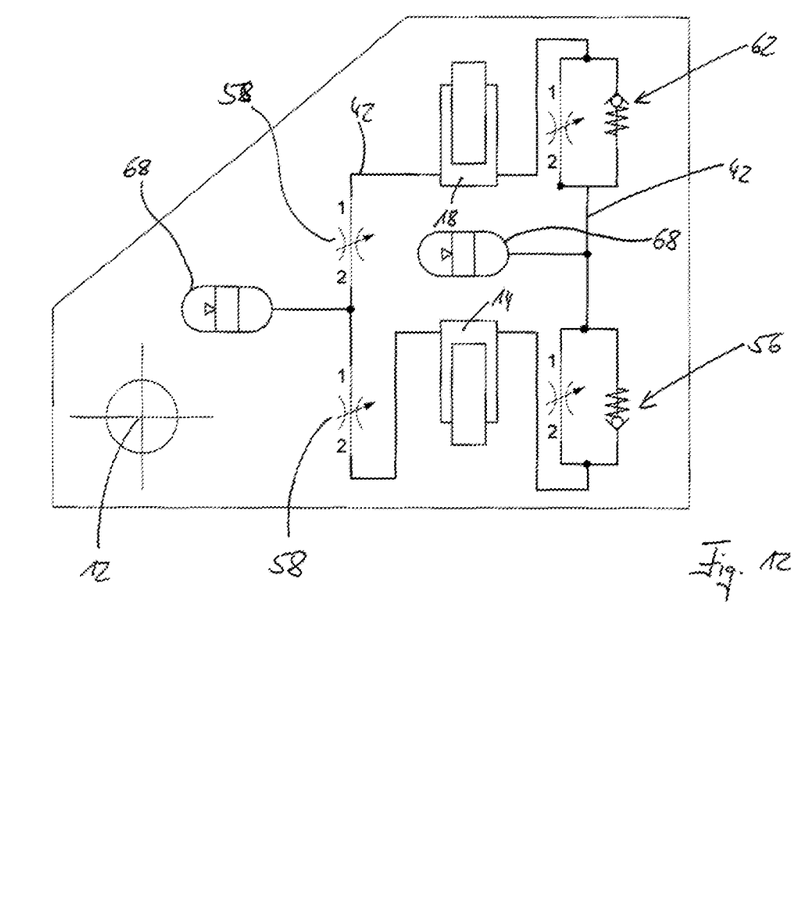

FIG. 12 shows a further embodiment in which the two cylinders 14, 18 are connected to one another via two fluid connections 42. The first damping device 56 and the second damping device 62 are located in the first fluid connection 42, which is shown on the right in FIG. 12. A pressure accumulator 68 is arranged in the middle. Two throttles 58 are arranged in the second fluid connection 42, which is shown on the left in FIG. 12, between which a pressure accumulator 68 is also arranged. Some or all of the shown throttles 58 and valves may be switched electrically or electronically, for example. This may be carried out using an electrical or electronic control (not shown), which processes measurement data recorded by sensors and detects, for example, states of movement of the ankle joint. In this way, the pressure accumulators 68 may be used as energy accumulators in which, for example, energy may be stored from a heel strike and may be delivered again at a different point in time during a step by control of the valves. For example, energy may be provided during the pushing-off of the foot from the ground (e.g., plantarflexion).

We claim:

1. An artificial ankle joint, comprising:
    a foot connector;
    a lower leg connector, the lower leg connector and the foot connector being pivotable with respect to another about an axis of rotation;
    a fluid system, comprising:
        a first cylinder having a first fluid chamber;
        a first piston movably positioned inside the first cylinder;
        a second cylinder having a second fluid chamber;
        a second piston movably positioned inside the second cylinder;
        a fluid connection providing fluid communication between the first fluid chamber and the second fluid chamber;
        a fluid movable from one of the first fluid chamber and the second fluid chamber through the fluid connection into the other of the first fluid chamber and the second fluid chamber by pivoting the foot connector relative to the lower leg connector about the axis of rotation;
    wherein the first cylinder and the second cylinder are positioned posterior of the axis of rotation.

2. The artificial ankle joint according to claim 1, wherein the fluid system further comprises a reservoir coupled to the first fluid chamber and to the second fluid chamber.

3. The artificial ankle joint according to claim 1, wherein at least one of the first cylinder and the second cylinder is a rotary cylinder.

4. The artificial ankle joint according to claim 1, further comprising a non-electronic controlling device operable to control an amount of the fluid that is moved between the first fluid chamber and the second fluid chamber based on at least one of a position or a change of position of the foot connector relative to the lower leg connector.

5. The artificial ankle joint according to claim 4, wherein the controlling device comprises a valve that is adapted to close the fluid connection when the foot connector is in a predetermined closing position relative to the lower leg connector.

6. The artificial ankle joint according to claim 5, wherein the controlling device further comprises a damper adapted to dampen a movement of the valve.

7. The artificial ankle joint according to claim 5, wherein the controlling device further comprises a contact surface and at least one contact element, the contact element sliding or rolling on the contact surface when the foot connector is moved relative to the lower leg connector, which leads to a movement of the valve.

8. An artificial ankle joint, comprising:
    a foot connector;
    a lower leg connector, the lower leg connector and the foot connector being pivotable with respect to each other about an axis of rotation;
    a fluid system, comprising:
        a first piston/cylinder assembly having a first fluid chamber and being positioned posterior of the axis of rotation;
        a second piston/cylinder assembly having a second fluid chamber and being positioned posterior of the axis of rotation;
        a fluid connection providing fluid communication between the first and second fluid chambers;
        a fluid movable between the first and second fluid chamber via the fluid connection when the foot connector rotates relative to the lower leg connector.

9. The artificial ankle joint according to claim 8, wherein the fluid system further comprises a reservoir in fluid communication with the first and second fluid chambers.

10. The artificial ankle joint according to claim 8, wherein at least one of the first and second piston/cylinder assemblies includes a rotary cylinder.

11. The artificial ankle joint according to claim 8, further comprising a non-electronic controlling device operable to control an amount of the fluid that is moved between the first and second fluid chambers when the foot connector rotates relative to the lower leg connector.

12. The artificial ankle joint according to claim 11, wherein the controlling device comprises a valve adapted to close the fluid connection when the foot connector is in a predetermined closing position relative to the lower leg connector.

13. The artificial ankle joint according to claim 12, wherein the controlling device further comprises a damper adapted to dampen a movement of the valve.

14. The artificial ankle joint according to claim 12, wherein the controlling device further comprises a contact surface and at least one contact element, the contact element sliding or rolling on the contact surface when the foot connector is moved relative to the lower leg connector, which leads to a movement of the valve.

15. The artificial ankle joint according to claim 8, wherein the first piston/cylinder assembly includes a first piston movable within a first cylinder, and the second piston/cylinder assembly includes a second piston movable within a second cylinder.

* * * * *